US009282406B2

(12) United States Patent
Bogason et al.

(10) Patent No.: US 9,282,406 B2
(45) Date of Patent: Mar. 8, 2016

(54) DIGITAL MICROPHONE WITH FREQUENCY BOOSTER

(71) Applicant: Knowles Electronics, LLC, Itasca, IL (US)

(72) Inventors: Gudmundur Bogason, Lejre (DK); Henrik Thomsen, Holte (DK)

(73) Assignee: KNOWLES ELECTRONICS, LLC, Itasca, IL (US)

( * ) Notice: Subject to any disclaimer, the term of this patent is extended or adjusted under 35 U.S.C. 154(b) by 138 days.

(21) Appl. No.: 14/132,471

(22) Filed: Dec. 18, 2013

(65) Prior Publication Data

US 2014/0177874 A1 Jun. 26, 2014

Related U.S. Application Data

(60) Provisional application No. 61/739,308, filed on Dec. 19, 2012.

(51) Int. Cl.

| | |
|---|---|
| ***H04R 3/00*** | (2006.01) |
| ***H04R 5/00*** | (2006.01) |
| ***A61F 11/06*** | (2006.01) |
| ***G10K 11/16*** | (2006.01) |
| ***H03B 29/00*** | (2006.01) |
| ***H04R 3/04*** | (2006.01) |
| ***H04R 1/00*** | (2006.01) |

(52) U.S. Cl.
CPC .................. *H04R 3/04* (2013.01); *H04R 1/005* (2013.01); *H04R 2201/003* (2013.01); *H04R 2410/03* (2013.01)

(58) Field of Classification Search
CPC .............. H04R 3/00; H04R 3/04; H04R 1/08; H04R 17/02
USPC .................... 381/111, 67, 26, 71.1, 71.14, 56
See application file for complete search history.

(56) References Cited

U.S. PATENT DOCUMENTS

| | | | | |
|---|---|---|---|---|
| 2003/0108209 | A1 | 6/2003 | McIntosh | |
| 2008/0013747 | A1 * | 1/2008 | Tran | 381/67 |
| 2008/0075306 | A1 | 3/2008 | Poulsen et al. | |
| 2011/0090338 | A1 | 4/2011 | Deline et al. | |

FOREIGN PATENT DOCUMENTS

| | | | |
|---|---|---|---|
| KR | 10-2011-0087696 | A | 8/2011 |
| KR | 10-2012-0074610 | A | 7/2012 |

OTHER PUBLICATIONS

International Search Report and Written Opinion for PCT/US2013/076100, dated Mar. 27, 2014, 15 pages.
Janssen et al., Look Ahead Based Sigma-Delta Modulation, Chapter 2: "Basics of Sigma-Delta Modulation," 2011, 25 pages.

* cited by examiner

*Primary Examiner* — Thjuan K Addy
(74) *Attorney, Agent, or Firm* — Fitch, Even, Tabin & Flannery LLP

(57) ABSTRACT

A digital microphone, the microphone includes a microelectromechanical (MEMS) component and a frequency boost component. The MEMS component is configured to convert. sound into an electrical signal. The frequency boost component is configured to receive the electrical signal and ultrasonically boost the electrical signal to create a frequency response. The frequency response does not substantially affect an audio band of interest of the microphone.

8 Claims, 4 Drawing Sheets

DIGITAL MICROPHONE WITH FREQUENCY BOOSTER

CROSS-REFERENCE TO RELATED APPLICATION

This patent claims benefit under 35 U.S.C. §119 (e) to U.S. Provisional application No. 61/739,308, filed Dec. 19, 2012 and entitled "Digital Microphone with Frequency Boost," the contents of which are incorporated herein by reference in their entirety.

TECHNICAL FIELD

This application relates to acoustic devices and, more specifically, to microphones that boost certain frequency ranges.

BACKGROUND OF THE INVENTION

Various types of microphones have been used through the years. In these devices, different electrical components are housed together within a housing or assembly. For example, a microphone typically includes a diaphragm and a back plate (among other components) and these components are disposed together within a housing. Other types of acoustic devices such as receivers may include other types of components.

After the signal from the MEMS components is obtained, other processing is sometimes performed. For example, noise shaping is typically performed on the signal received from the MEMS components.

Current MEMS microphones are also coupled to other applications such as those associated with a personal computer or cellular phone. In order to interface with these applications, certain performance standards need to be met. In one example and with respect to the noise shaping that occurs, outputs from the processing with a fourth order noise shaping component have to be made compliant with existing chipsets and codecs. Unfortunately, in previous systems this has meant that some frequencies in the microphone signal (e.g., ultrasonic frequencies) are seriously corrupted by noise.

One previous way of combating this problem was to increase the clock frequency. However, this approach has proved unsatisfactory because it increased the current consumption of the system to an unacceptable level and potentially reduced the audio performance of the system.

BRIEF DESCRIPTION OF THE DRAWINGS

For a more complete understanding of the disclosure, reference should be made to the following detailed description and accompanying drawings wherein.

Skilled artisans will appreciate that elements in the figures are illustrated for simplicity and clarity. It will further be appreciated that certain actions and/or steps may be described or depicted in a particular order of occurrence while those skilled in the art will understand that such specificity with respect to sequence is not actually required. It will also be understood that the terms and expressions used herein have the ordinary meaning as is accorded to such terms and expressions with respect to their corresponding respective areas of inquiry and study except where specific meanings have otherwise been set forth herein.

DETAILED DESCRIPTION

Microelectromechanical (MEMS) microphones having ultrasonic boosting are provided. These approaches provide a noise shaping characteristic compliant with chipsets and codecs. The approaches described herein maintain a frequency response that is independent of the external clock frequency and this enables precise transition between the audio and ultrasonic frequency bands. Also the ultrasonic signals are raised above the noise shaped quantization noise floor while avoiding overload due to ultrasonic jammers in the environment where the microphone operates. Another advantage involves group delay. Group delay involves the use of multiple microphones to determine a position of an object based upon the time delay of signals received. If a random delay were inserted into the signal, this functionality would not work. The present approaches avoid inserting random delay and avoid these problems.

Figure 1:
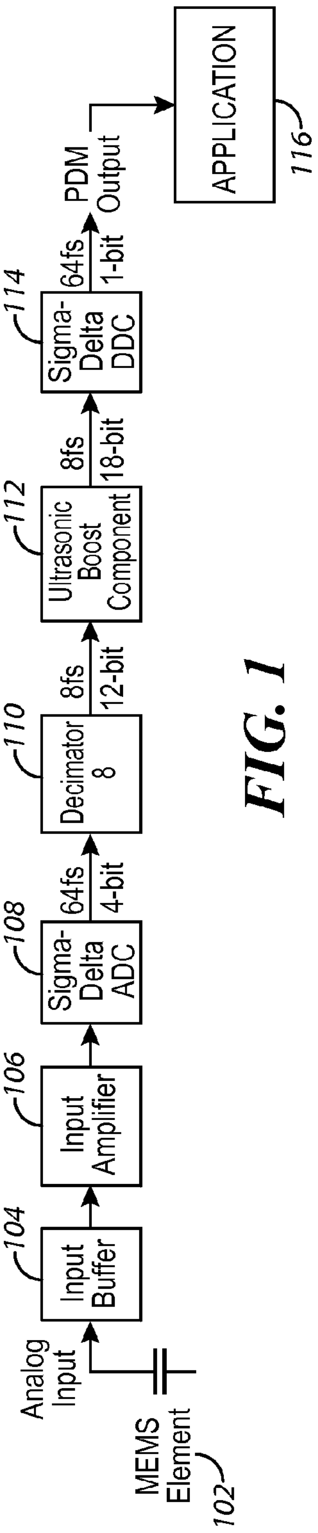
FIG. 1 comprises a block diagram of a system providing ultrasonic boosting according to various embodiments of the present invention.

Referring now to FIG. 1, one example of a system that provides ultrasonic boosting is described. The system includes a MEMS component 102, an input buffer 104, an input amplifier 106, a Sigma-Delta ADC 108, a decimator 110, a frequency booster component 112, a Sigma Delta digital-to-digital converter 114, and an application 116.

The MEMS component 102 includes, for example, a back plate, diaphragm, supporting structure. The component 102 converts sound into an analog electrical signal.

The function of the input buffer 104 is to interface the MEMS element to the remaining blocks while maintaining a high SNR and low signal loss. The function of the input amplifier 106 is to amply the signals to acceptable levels.

The Sigma-Delta ADC 108 in one example implements a third order noise shaping resulting in a quantization noise increase of approximately 60 dB/dec, which is sufficiently low in order not to corrupt the ultrasonic signals significantly. As used herein, "order" refers to how steep the cutoff is in the frequency response. In order to obtain sufficiently acceptable audio performance with the third order noise shaping, the Sigma-Delta ADC 202 contains a multi-bit quantizer with quantization codes in the range −4−3, . . . , 0, . . . , +3, +4. An added benefit of using the mentioned multi-bit quantizer is that the Sigma-Delta ADC 202 becomes very stable and handles overload situations with low distortion. The Sigma-Delta ADC 202 receives an analog signal and produces a 4-bit, 64 fs signal.

The decimator 110 is a decimate by 8 block that reduces the sampling rate from 3072 kHz to 3072 kHz/8=384 kHz resulting in a Nyquist bandwidth limiting of 192 kHz. In other words, the decimator 110 is used to slow down the data rate. Bits are added to maintain the same information content at a lower rate. There are various reasons for accomplishing this. For instance, by reducing the sampling rate by a factor of 8 it is possible to implement the ultrasonic boost filter 206 (see below) with good balance between computational cycle requirements and parallelism in order to minimize current consumption and gate count. Another reason is to remove any high frequency noise above the ultrasonic band from entering the digital signal path. The decimator 110 takes the signal from the Sigma-Delta ADC 108 and converts it to a 12 bit, 8 fs signal.

The frequency booster component 112 provides ultrasonic boosting for signals. This functionality may be performed by any combination of hardware and software and may be configured in various ways. For example, the frequency booster component 112 may be located on a chip or on multiple chips. This component is described in greater detail elsewhere herein.

The Sigma-Delta DDC 114 performs, for example, a fourth order noise shaping in order to deliver a PDM bit stream that has the properties expected by the external chipsets and codecs. The Sigma-Delta DDC 114 creates a 1-bit, 64 fs signal is an output.

The application 116 is any application that utilizes the signal from the MEMS 102 that has been processed by the frequency booster component 112. For example, the application 116 may be a cellular phone application or an application in a personal computer. Other examples of applications are possible.

In other aspects, the boost frequency component 112 could be placed in the analog domain in front of the A/D (or Sigma Delta) converter 108 as an analog high pass filter. In this case, the frequency response will be produced clock frequency independent.

In some aspects, the boost component frequency response is independent of the clock so that the boost filter should not affect the audio band or the band of interests. In this respect, the digital filter is updated when the clock frequency changes.

Figure 2:
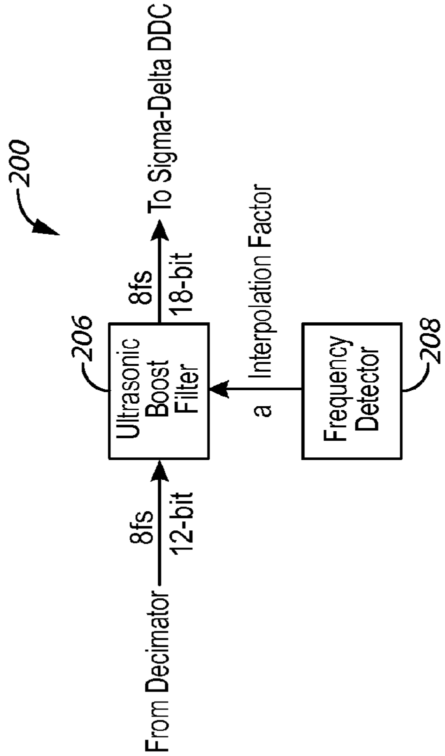
FIG. 2 comprises a block diagram of a frequency boost component according to various embodiments of the present invention.

Referring now to FIG. 2, a frequency booster component 200 (e.g., the frequency booster component 112 in FIG. 1) is described in detail. The frequency booster component 200 includes an ultrasonic boost filter 206, and a frequency detector 208. The frequency response produced by the circuit 200 is not dependent upon an external clock. In this respect, it is not desirable for a variable external clock to be able to affect the filter response. If this were to occur, the frequency response of the audio band might be disturbed by the ultrasonic frequency response or the ultrasonic frequency response might be shifted up to high and the filtering would not work.

In the example described herein, the digital microphone ASIC is clocked by an external clock frequency of approximately 3072 kHz. It will be appreciated that other frequencies are possible.

The ultrasonic boost filter 206 in this example implements a 16th order digital FIR filter with a kind of high-pass frequency response that is 0 dB in the audio band and with a configurable boosting of the gain in the ultrasonic band in steps of 0 dB, +7 dB, +11 dB and +15 dB. Other examples of steps and values for these steps are possible. This configurable boosting makes it possible to make trade offs between how much the ultrasonic signals can/must be raised above the noise shaped quantization noise in the Sigma-Delta DDC 114 while at the same time avoiding overload due to ultrasonic jammers in the environment where the microphone operates.

When the boost filter is implemented in the digital domain, the quantization noise +KT/C in the ultra sound band of the A/D converter is preferably lower than the quantization noise of the Sigma-Delta DDC in the ultra sound band. If this condition is not true, digital boosting of the ultra sound band may not improve the ultra sound SNR.

By using a FIR filter it is ensured that the phase response is linear with frequency and that the group delay is constant. Advantageously, this ensures that there are no delay differences between several microphones that otherwise might deteriorate the positioning resolution of the ultrasonic gesture detection algorithms. Normally, the frequency response of a digital filter scales directly with the clock frequency. This is however not acceptable in some situations. Therefore, the ultrasonic boost filter 206 is able to recalculate the FIR filter coefficients based on an interpolation value from the frequency detector 208 in order to maintain a constant frequency response for all external frequencies in the range 3072 kHz . . . 4800 kHz. As mentioned, in one aspect the boost filter 206 uses a Finite Impulse Response filter. However, in other examples an Infinite Impulse Response filter can be used. The boost filter creates an 18 bit, 8 fs signal in this example. In other examples, the response of the filter need not be linear as long as the responses are identical for two (or more) microphones.

The frequency detector 208 performs several tasks. One function performed is the calculation of an interpolation factor that is a value between 0 and 1 and that is used by the ultrasonic boost filter 206 to recalculate the FIR filter coefficients in order to maintain frequency response that is independent of the external dock frequency. An interpolation value of 0 exists for external frequencies up to 3072 kHz. After that, it increases linearly with frequency and saturates at 1 at an external frequency of 4800 kHz.

Figure 3:
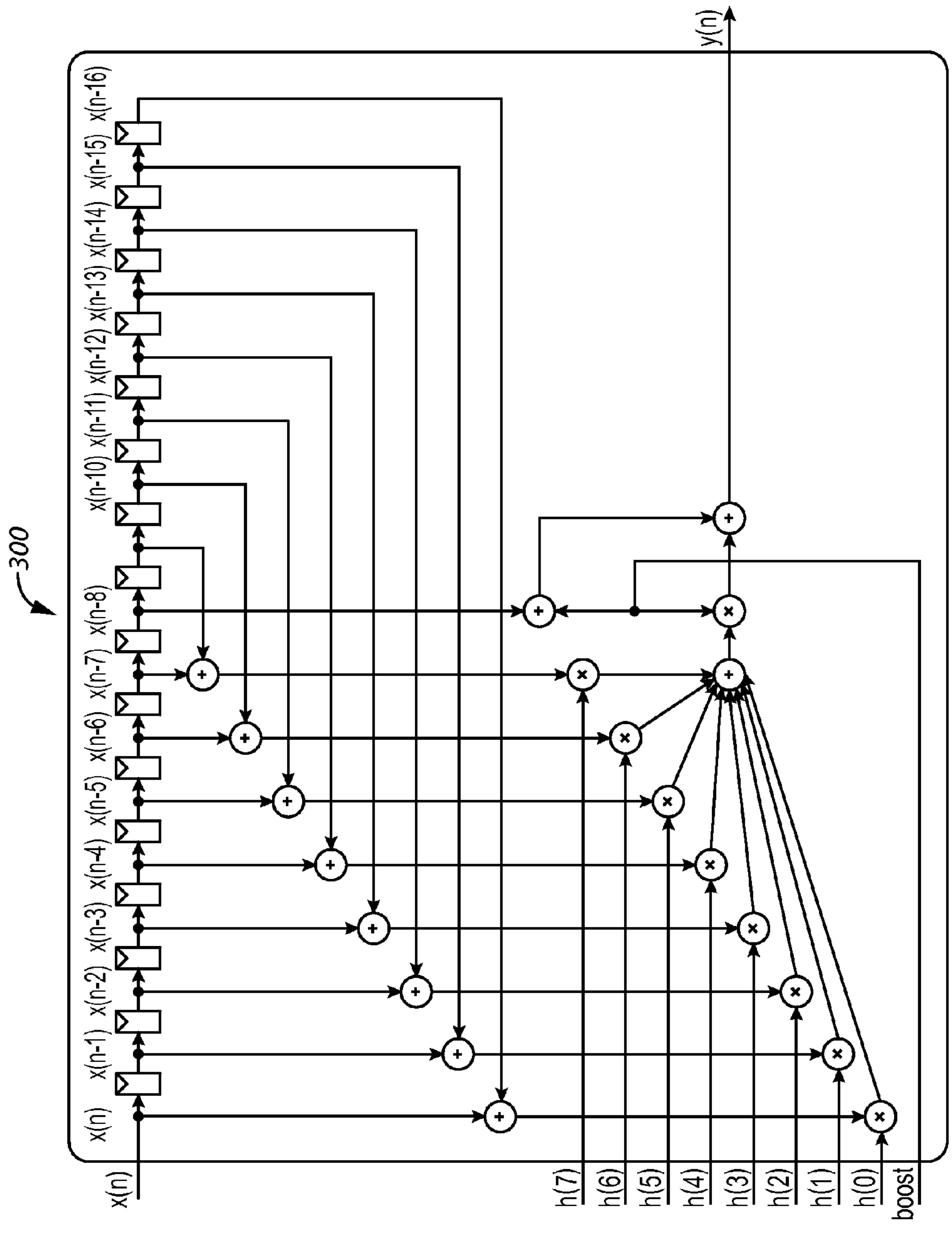
FIG. 3 comprises a block diagram of a FIR filter within the boost filter according to various embodiments of the present invention.
Figure 4:
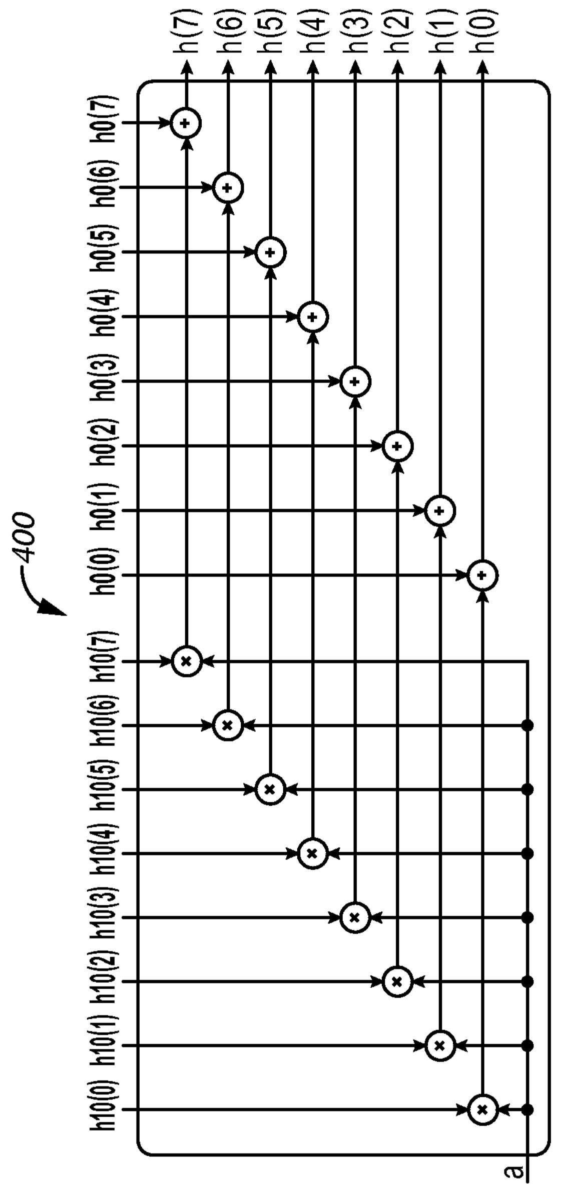
FIG. 4 comprises a block diagram of an interpolation block within the boost filter according to various embodiments of the present invention.

Referring now to FIG. 3 and FIG. 4, aspects of two functions present in ultrasonic boost filters are described. The ultrasonic boost filter includes a high-pass FIR filter 300 for boosting the ultrasonic frequencies added together with the audio frequencies. In this example, this high-pass boosting FIR filter is implemented as a $16^{th}$ order filter meaning that it contains 17 filter coefficients and 16 delay elements. The output (y(n)) of the FIR filter 300 is represented as:

$$y(n)=h(0)*x(n)+h(1)*x(n-1)+\ldots+h(8)*x(n-8)+\ldots+h(15)*x(n-15)+h(16)*x(n-16) \quad (1)$$

The filter coefficients, [h(0), h(1), . . . , h(15), h(16)], are symmetrical around the center coefficient h(8): h(0)=h(16), h(1)=h(15), and this can be used to reduce the number of multiplications and to reduce the number of coefficients that need to be stored:

$$y(n)=h(0)*[x(n)+x(n-16)]+h(1)*[x(n-1)+x(n-15)]+\ldots+h(7)*[x(n-7)+x(n-9)]+h(8)*x(n-8) \quad (2)$$

To simplify the implementation the filter coefficients are normalized so that the center tap h(8) becomes equal to 1. The output (y(n)) of this normalized FIR filter is represented as:

$$y(n)=h(0)*[x(n)+x(n-16)]+h(1)*[x(n-1)+x(n-15)]+\ldots+h(7)*[x(n-7)+x(n-9)]+x(n-8) \quad (3)$$

The boosted high-pass FIR filter added together with the audio frequencies is therefore represented as:

$$y(n)=\text{boost}*[h(0)*[x(n)+x(n-16)]+h(1)*[x(n-1)+x(n-15)]+\ldots+h(7)*[x(n-7)+x(n-9)]+x(n-8)]+x(n-8) \quad (4)$$

This can be represented as:

$$y(n)=\text{boost}*[h(0)*[x(n)+x(n-16)]+h(1)*[x(n-1)+x(n-15)]+\ldots+h(7)*[x(n-7)+x(n-9)]]+(1+\text{boost})*x(n-8). \quad (5)$$

FIG. 3 shows the implementation of equation (5).

The filter coefficients for the FIR filter 300 need to be updated whenever the clock frequency for the FIR filter is changed in order to maintain a frequency response that is independent of the clock frequency. The FIR filter 300 in this example is intended to operate with clock frequencies in the range 3072 kHz to 4800 kHz. In this frequency range, the filter coefficients change continuously in such a way so that they can be approximated with sufficient accuracy by interpolating between two sets of coefficient, one for a clock frequency of 3072 kHz and another for a clock frequency of 4800 kHz.

The set of filter coefficients [h0(0), h0(1), . . . , h0(7)] for a clock frequency of 3072 kHz and the set of filter coefficients [h1(0), h1(1), . . . , h1(7)] for a clock frequency of 4800 kHz can be used to interpolate the FIR filter coefficients in the following way:

$$h(n)=(1-a)*h0(n)+a*h1(n), n=0,1, \ldots ,7 \quad (6)$$

The above equation can be written as:

$$h(n)=h0(n)+a*[h1(n)-h0(n)], n=0,1, \ldots ,7 \quad (7)$$

The above equation can be written as:

$$h(n)=h0(n)+a*h10(n), h10(n)=h1(n)-h0(n), n=0,1, \ldots ,7 \quad (8)$$

Equation (8) is implemented as the apparatus 400 shown in FIG. 4. In other words, the filter coefficients [h0(0), h0(1), . . . , h0(7)] can be determined according to this approach.

Figure 5:
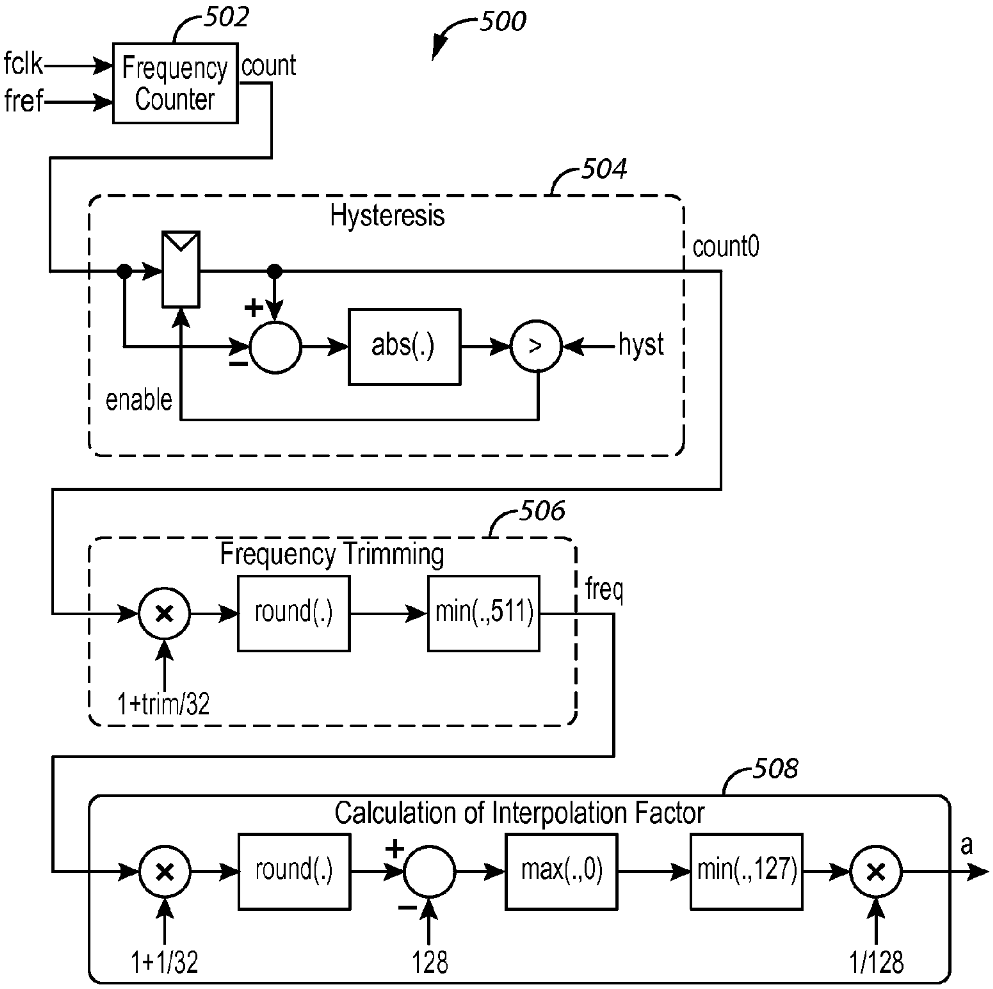
FIG. 5 comprises a block diagram of a frequency detector according to various embodiments of the present invention.

Referring now to FIG. 5, one example of a frequency detector 500 is described. The frequency detector 500 calculates the interpolation factor based on the external clock frequency fclk. The frequency detector 500 includes a frequency counter 502, a hysteresis block 504, a frequency trimming block 506, and a calculation of interpolation factor block 508.

The frequency counter 502 receives a reference frequency fref and a clock frequency fclk. The output of the Frequency Counter is given by:

$$\text{count}=\text{fclk}/\text{fref} \quad (9)$$

Where fref is a frequency from an internal reference oscillator. In one example, the nominal frequency of this oscillator is: fref=13.89 kHz. So, to take one example, with fclk=2400 kHz, 3072 kHz, 4800 kHz, the count=173, 221, 346.

The count output will be toggling around a nominal value and it is necessary to apply some hysteresis to remove this. The hysteresis block 504 contains a count0 value that is updated to be equal to the count value only if the following condition is true:

$$\text{abs}(\text{count}-\text{count0})>\text{hyst} \quad (10)$$

The frequency trimming block 506 is used to indirectly trim the frequency fref of the internal reference oscillator in case it deviates from the nominal value. The output of the frequency trimming block 406 is therefore given by:

$$\text{freq}=\min(\text{round}(\text{count0}*(1+\text{trim}/32)),511) \quad (11)$$

In case the internal reference frequency deviates from the expected value it is trimmed by selecting a proper value from the trim parameter. Normally the trim parameter is 0, count0=173, 221, 346=>freq=173, 221, 346. The trimmed frequency is now used to calculate the interpolation factor using the following relationship:

$$a=\min(\max(\text{round}(\text{freq}*(1+1/32))-228,0),127)/128 \quad (12)$$

For example, when freq=173, 221, 346 then $a$=0, 0, 0.9921875.

Figure 6:
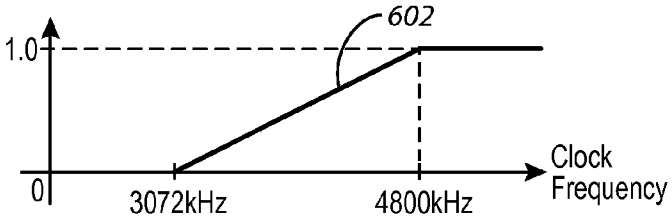
FIG. 6 comprises a chart showing an interpolation value versus frequency according to various embodiments of the present invention.

Referring to FIG. 6, one example of the interpolation factor as a function of external clock frequency is described. As shown, a interpolation factor line 602 is a linear value between 0 and 1.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A digital microphone, the digital microphone comprising:

a microelectromechanical (MEMS) component, the MEMS component configured to convert sound into an electrical signal; and an integrated circuit including a frequency boost component, the frequency boost component configured to receive the electrical signal and boost ultrasonic frequency bands within the electrical signal in at least one predetermined step to create a frequency response, the integrated circuit configured to receive a clock external to the digital microphone, the frequency response not substantially affecting an audio band of interest of the microphone, wherein the frequency response is independent of the clock external to the digital microphone.

2. The digital microphone of claim 1, wherein the frequency boost component comprises an ultrasonic boost filter and a frequency detector.

3. The digital microphone of claim 2, wherein the digital microphone includes a sigma-delta analog-to-digital converter and a sigma-delta digital-to digital converter, and wherein the boost filter is implemented in the digital domain, and wherein a first quantization noise in an ultra sound band of the sigma-delta analog-to-digital converter is lower than the a second quantization noise of the sigma-delta digital-to digital converter in the ultra sound band.

4. The digital microphone of claim 1, wherein the MEMS component comprises a back plate and a diaphragm.

5. The digital microphone of claim 1, wherein the digital microphone is configured to couple to an application.

6. The digital microphone of claim 1, further comprising a sigma-delta digital-to digital converter that receives the frequency response.

7. The digital microphone of claim 1, further comprising a sigma-delta analog-to-digital converter.

8. The digital microphone of claim 1, wherein the frequency boost component raises the frequency response above a noise-shaped quantization noise floor.

* * * * *